United States Patent [19]
Hinkson et al.

[11] 3,931,351
[45] *Jan. 6, 1976

[54] MODIFICATION OF IRON AND BARIUM FERRITE CATALYSTS

[75] Inventors: Robert E. Hinkson; William H. Taylor, both of Houston, Tex.

[73] Assignee: Petro-Tex Chemical Corporation, Houston, Tex.

[ * ] Notice: The portion of the term of this patent subsequent to June 13, 1989, has been disclaimed.

[22] Filed: Aug. 1, 1974

[21] Appl. No.: 493,494

Related U.S. Application Data

[60] Division of Ser. No. 400,755, Sept. 26, 1973, Pat. No. 3,852,370, which is a continuation-in-part of Ser. No. 249,963, May 3, 1972, abandoned.

[52] U.S. Cl. ........................ 260/680 D; 260/683.3
[51] Int. Cl.² ........................................... C07C 5/48
[58] Field of Search .................... 260/680 D, 680 E

[56] References Cited
UNITED STATES PATENTS

| | | | |
|---|---|---|---|
| 3,207,806 | 9/1965 | Bajars | 260/680 D |
| 3,207,809 | 9/1965 | Bajars | 260/680 D |
| 3,308,193 | 3/1967 | Bajars | 260/680 D |
| 3,308,198 | 3/1967 | Bajars | 260/680 D |
| 3,670,042 | 6/1972 | Croce et al. | 260/680 E |

*Primary Examiner*—Paul M. Coughlan, Jr.
*Attorney, Agent, or Firm*—N. Elton Dry; Kenneth H. Johnson

[57] ABSTRACT

Catalysts comprising ferrites of iron modified with oxides of cerium, zinc, manganese and lead and ferrites of barium modified with oxides of zinc, manganese and lead and a process of oxidative dehydrogenation of organic compounds in the presence of these catalysts compositions and cocatalyst such as chlorine.

5 Claims, No Drawings

MODIFICATION OF IRON AND BARIUM FERRITE CATALYSTS

CROSS REFERENCE

This application is a division of Ser. No. 400,755 filed Sept. 26, 1973, U.S. Pat. No. 3,852,370 which was a continuation in part of Ser. No. 249,963 filed May 3, 1972, and now abandoned.

BACKGROUND OF THE INVENTION

1. Field of the Invention

This application relates to the oxidative dehydrogenation of organic compounds in the presence of oxygen, halogen and a particular catalyst. The catalyst of this invention comprises those selected from the group consisting of iron ferrite which has been modified by the addition thereto of a metal oxide comprising the oxides of cerium, zinc, manganese and lead and barium ferrite which has been modified by the addition thereto of a metal oxide comprising the oxides of zinc, manganese and lead.

2. Description of the Prior Art

U.S. Pat. No. 3,303,234 discloses the oxidative dehydrogenation of organic compounds with a catalyst comprising barium ferrite. The oxidative dehydrogenation of organic compounds with catalyst comprising ferrites is also disclosed in U.S. Pat. Nos. 3,270,080; 3,284,536; 3,303,235; 3,303,236; 3,303,238; 3,308,182; 3,324,195; 3,334,152; 3,342,890; 3,420,911; 3,420,912; 3,428,703 and 3,440,229.

SUMMARY OF THE INVENTION

This invention relates to improved catalyst compositions and a process for oxidative dehydrogenation of organic compounds using the improved catalyst. The improved catalyst compositions comprise ferrites of iron having combined therewith as a catalyst modifier a metal oxide selected from the group consisting of $CeO_2$, $ZnO$, $MnO_2$ and $PbO$ or mixtures of these oxides and ferrites of barium having combined therewith as a catalyst modifier a metal oxide selected from the group consisting of $ZnO$, $MnO_2$ and $PbO$ or mixtures of these oxides. This invention also relates to a process where these improved catalyst compositions are used in an oxidative dehydrogenation process where oxyge, an organic compound and a halogen are fed to a reactor containing the improved catalyst compositions.

DESCRIPTION OF THE PREFERRED EMBODIMENT

According to this invention an improved catalyst and a process utilizing the improved catalyst are provided for the dehydrogenation of aliphatic organic compounds to obtain corresponding unsaturated derivatives thereof. One of the primary objectives in catalyst development is to produce more active catalysts which retain a high degree of selectivity of the products desired. Such catalysts generally provide improved processes resulting in higher yields of the desired product.

The catalyst of the present invention comprise iron ferrite in which there has been incorporated a promoting amount of a metal oxide selected from the group consisting of $CeO_2$, $ZnO$, $MnO_2$, $PbO$ and mixtures thereof, and barium ferrite in which there has been incorporated a promoting amount of a metal oxide selected from the group consisting of $ZnO$, $MnO_2$, $PbO$ and mixtures thereof. The improved process of the present invention comprises feeding oxygen or an oxygen containing gas, a halogen and the organic compound to be dehydrogenated to a reactor containing the iron ferrite or barium ferrite which has been modified as specified above by the addition of a promoting amount of an oxide of the metals, cerium, zinc, manganese and lead. The iron ferrite and barium are known commercial products in the improved catalyst of the present invention, the iron ferrite or barium ferrite component will form a major proportion of the catalyst composition with the metal oxide promoter being present in a minor proportion. Thus, the catalyst composition of the present invention can contain up to 45 percent by weight cerium oxide, zinc oxide, manganese oxide, lead oxide, or mixtures thereof with the remainder being essentially iron ferrite, barium ferrite or mixtures thereof. Generally, it has been found preferable to incorporate from 0.35 to 1.3 moles of the metal oxide modifier per mole of iron oxide or barium oxide in the catalyst composition.

The organic compounds to be dehydrogenated according to the process of this invention are hydrocarbons of 4 to 7 carbon atoms and preferably hydrocarbons selected from the group consisting of saturated hydrocarbons, cycloaliphatics, monoolefins, diolefins and mixtures thereof of 4 to 5 or 6 carbon atoms having a straight chain of at least 4 carbon atoms. Examples of preferred feed materials are butene-1, cis-butene-2, trans-butene-2, 2-methyl butene-1, 2-methyl butene-2, 3-methyl butene-1, n-butane butadiene-1,3, methyl butane, cyclohexane, cyclohexene, 2-methyl pentene-1, 2-methyl pentene-2 and mixtures thereof. For example, n-butane may be converted to a mixture of butene-1 and butene-2 or may be converted to a mixture of butene-1, butene-2 and/or butadiene-1,3. A mixture of n-butane and butene-2 may be converted to butadiene-1,3 or to a mixture of butadiene-1,3 together with some butene-2 and butene-1. Vinylacetylene may be present as a product, particularly when butadiene-1,3 is used as a feedstock. Thus, the process of this invention is useful in converting hydrocarbons to less saturated hydrocarbons of the same number of carbon atoms. The major proportion of the hydrocarbons converted will be to less saturated hydrocarbons of the same number of carbon atoms. Particularly, the preferred products are butadiene-1,3 and isoprene. Useful feeds may be mixed hydrocarbon streams such as refinery streams, or the olefin containing hydrocarbon mixture obtained as the product from the dehydrogenation of hydrocarbons. In the production of gasoline from higher hydrocarbons either thermal or catalytic cracking a hydrocarbon stream containing predominantly hydrocarbons of four carbon atoms may be produced and comprise a mixture of butenes together with butadiene, butane, isobutane, isobutylene and other ingredients in minor amounts. These and other refinery by-products which contain normal, ethylenically unsaturated hydrocarbons are useful as starting materials for the present process. Although various mixtures of hydrocarbons are useful, the preferred hydrocarbon feed contains at least 50 weight percent of a hydrocarbon selected from the group consisting of butene-1, butene-2, n-butane, butadiene-1,3, 2-methyl butene-1, 2-methyl butene-2, 2-methyl butene-3 and mixtures thereof, and more preferably contains at least 70 weight percent, of one or more of these hydrocarbons (with both of these percentages being based on the total weight of the organic composition of the feed to the reactor). Any remainder may be, for example, essentially aliphatic hydrocarbons. This invention is particularly useful to provide a process whereby the major product of the hydrocarbon converted is a dehydrogenated hydrocarbon product having the same number of carbon atoms as the hydrocarbon fed.

Diluents such as nitrogen, helium, or other gases which are not dehydrogenated or which are dehydrogenated only to a limited extent may be used in the process of the present invention. Mixtures of diluents may also be employed.

The halogen fed to the dehydrogenation zone may be either elemental halogen or any compound of halogen which would liberate under the conditions of reaction. Suitable sources of halogens are such as hydrogen iodide, hydrogen bromide. and hydrogen chloride; aliphatic halides such as ethyl iodide, methyl bromide, 1,2-dibromo ethane, ethyl bromide, amyl bromide and allyl bromide; cyclo-aliphatic halides such as cyclohexylbromide; aromatic halides such as benzyl bromide; halohydrins such as ethylene bromohydrin; halogen substituted aliphatic acids such as bromoacetic acid; ammonium iodide; ammonium bromide; ammonium chloride; organic amine halide salts such a methyl amine hydrobromide; and the like. Mixtures of various sources of halogens may be used. The preferred sources of halogen are iodine, bromine and chlorine and compounds thereof such a hydrogen bromine, hydrogen iodide, hydrogen chloride, ammonium bromide, ammonium iodide, ammonium chloride, alkyl halides of 1 to 6 carbon atoms and mixtures thereof with the chloride compounds being particularly preferred, with excellent results being obtained from the use of chlorine or hydrogen chloride. When terms such as halogen liberating materials or halogen materials are used in the specification and claims, this includes any source of halogen such as elemental halogen, hydrogen halides or ammonium halides. The amount of halogen calculated as elemental halogen, may be as little as about 0.0001 or less mole of halogen per mole of the hydrocarbon compound to be dehydrogenated to as much as 0.2 or 0.5 moles of halogen per mole of hydrocarbon compound to be dehydrogenated. The preferred range is from 0.0001 to 0.09 moles of halogen per mole of hydrocarbon to be dehydrogenated.

Oxygen will be present in the reaction zone in an amount within the range of 0.2 to 2.5 moles of oxygen per mole of hydrocarbon to be dehydrogenated. Generally, better results may be obtained if the oxygen concentration is maintained between about 0.25 and about 1.6 moles of oxygen per mole of hydrogen to be dehydrogenated, such as between 0.35 and 1.3 moles of oxygen per mole of hydrocarbon to be dehydrogenated. The oxygen may be fed to the reactor as pure oxygen, as air, as oxygen-enriched air, oxygen mixed with diluents, etc. Based on the total gaseous mixture entering the reactor, the oxygen normally will be present in an amount from about 0.5 to 25 volume percent of the total gaseous mixture, and more usually will be present in an amount from about 1 to 50 volume percent of the total. The total amount of oxygen utilized may be introduced into the gaseous mixture entering the catalytic zone or it can be added in increments, such as different sections of the reactor. The above described proportions of oxygen employed are based on the total amount of oxygen used. The oxygen may be added directly to the reactor or it may be premixed, for example, with a diluent or steam.

The temperature for the dehydrogenation reaction will be greater than 400° C, and the maximum temperature in the reactor may be about 750° C or perhaps higher under certain circumstances. Excellent results are obtained within the range of about 500°C to 600°C. The temperatures are measured at the maximum temperature in the reactor.

The dehydrogenation reaction may be carried out at atmospheric pressure, super-atmospheric pressure or at sub-atmospheric pressure. The total pressure of the system will normally be about or in excess of atmospheric pressure although sub-atmospheric pressure may also desirably be used. Generally, the total pressure will be between about 4 psia and about 100 or 125 psia. Preferably the total pressure will be less than about 75 psia and excellent results will be otained at about atmospheric pressure.

Conveniently, the oxygen may be added as air with any nitrogen or other gas acting as a diluent for the system. Mixtures of diluents may be employed. Volatile compounds which are not dehydrogenated or which are dehydrogenated only to a limited extent may be present as a diluent.

The reaction mixture may contain a quantity of steam. The range generally being between about 2 to 40 moles of steam per mole of hydrocarbon to be dehydrogenated if steam is employed. The functions of the steam are several fold, as described in the patent references mentioned hereinbefore. However, the steam does act as a diluent. Diluents generally may be used in the same quantities specified for the steam. Excellent results are obtained when the gaseous composition fed to the reactor consists essentially of hydrocarbons, inert diluents and oxygen as the sole oxidizing agent.

The gaseous reactants may be conducted through the reaction chamber at a fairly wide range of flow rates. The optimum flow rate will be dependent upon such variables as the temperature of reaction, pressure, particle size and whether a fluid bed or a fixed bed reactor is utilized. Desirable flow rates may be established by one skilled in the art. Generally, the flow rates will be within the range of about 0.10 to 25 liqiud volumes of the hydrocarbon to be dehydrogenated per volume of reactor containing catalyst per hour (referred to as LHSV), wherein the volumes of hydrocarbon are calculated at standard conditions of 25° C and 760 millimeters of mercury. Usually, the LHSV will be between 0.15 and about 5 or 10. For calculation, the volume of reactor containing catalyst is that volume of reactor space excluding the volume displaced by the catalyst for example if a reactor has a particular volume of cubic feet of weight space, when that void space is filled with catalyst particles the original void space is the volume of reactor containing catalyst for the purpose of calculating the flow rate. The gaseous hourly space flow velocity (GHSV) is the volume of the hydrocarbon to be dehydrogenated in the form of vapor calculated under standard conditions of 25° C and 760 millimeters of mercury per volume of reactor space containing catalyst per hour. Generally, the GHSV will be between about 25 and 6400, and excellent results have been obtained between about 38 and 3800. Suitable contact times are, for example, from about 0.001 or higher to about 5 or 10 seconds with particularly good results being obtained between 0.01 and 3 seconds. The contact time is the calculated dwell time of the reaction mixture in the reaction zone, assuming the moles of product mixture are equivalent to the moles of feed mixture. For the purpose of calculation of residence times, the reaction zone is the portion of the reactor containing catalyst.

As mentioned hereinbefore, the catalyst composition of the present invention comprises iron ferrite or barium ferrite combined together with the specified metal oxide selected from the group consisting of $CeO_2$, ZnO, $MnO_2$, PbO and mixtures thereof. Based on the total active catalyst components, the metal oxide will be present in a range of 0.3 to 1.3 moles to mole of the ferrite component. The catalyst composition can also include inert binding agents and fillers, but these will not ordinarily exceed about 50 percent or 60 percent by weight of the catalytic composition including active catalyst components and inert binding agents or fillers. The catalyst will be by definition present in a catalytic amount. The amount of catalyst ordinarily will be greater than ten square feed of catalyst surface per cubic foot of reaction zone containing catalyst. The term catalyst is meant to mean total active catalyst components and does not include inert binding agents or fillers. Of course, the amount of catalyst may be much greater, particularly when irregular surface catalyst are used. When the catalyst is in the form of particles, either supported or unsupported, the amount of catalyst surface may be expressed in terms of the surface area per unit weight of any particular volume of catalyst particles. The ratio of catalyst surface to weight will be dependent upon several factors, including the particle size distribution, apparent bulk density of the particles, the carrier etc. Typical values for the surfaced to weight ratio are such as about one-half to 200 square meters per gram although higher and lower values may be used.

The dehydrogenation reactor may be of the fixed bed of fluid bed type. Conventional reactors for the production of unsaturated hydrocarbons are satisfactory. Excellent results have been obtained by packing the reactor with catalyst particles as the method of introducing the catalytic surface. The catalytic surface may be introduced as such or it may be deposited on a carrier by methods known in the art such as by preparing an aqueous solution or dispersion of a catalytic material and mixing the carrier with the solution or dispersion until the active ingredients are coated on the carrier. If a carrier is utilized, very useful carriers are silicon carbide, pumice and like. When carriers are used, the amount of catalyst on the carrier will generally be between about 5 to 75 weight percent of the total weight of active catalytic material plus carrier. Another method for introducing the required surface is to utilize as a reactor a small diameter tube wherein the tube wall is catalytic or is coated with catalytic material. Other methods may be utilized to introduce the catalytic surface such as by the use of rods, wires, mesh, or shreds and the like of catalytic material.

In the following examples will be found specific embodiments of the invention and details employed in the practice of the invention. Percent conversion refers to the moles of hydrocarbon consumed per 100 moles of hydrocarbon fed to the reactor, percent selectivity refers to the moles of product formed per 100 moles of hydrocarbon consumed, and percent yield refers to the moles of product formed per 100 moles of hydrocarbon fed. All other percentages are be weight unless expressed otherwise.

EXAMPLES 1–5

Barium ferrite (Columbian Carbon Company EG No. 4) was used as the catalyst in Example 1. In Examples 2 – 5 the oxides of zinc, manganese and lead were incorporated with the barium ferrite catalyst respectively in the amounts shown in Table I. The barium ferrite or barium ferrite containing the metal oxide was coated on 4 to 8 mesh alumina pellets in an amount of roughly 30 percent of weight of the barium ferrite or barium ferrite incorporating the metal oxide based on the total weight. In each of the Examples 1–5, n-butane was dehydrogenated at atmospheric pressure in a Vycor glass reactor containing therein a 50 cc. catalyst bed supported on a 1-inch deep layer of Rashig rings. The reactants, n-butane, oxygen, nitrogen and chlorine were introduced into the top of the glass reactor, and the effluent gases were withdrawn from the bottom of the reactor. Samples of the effluent gases were analyzed in a vapor chromatograph.

The mixture of n-butane, oxygen, nitrogen and chlorine was fed to the reactor in an amount of 1.3 moles of oxygen, 0.3 moles of chlorine and 15 moles of nitrogen per mole of n-butane. The LHSV was 0.25 and the maximum temperature in the reactor was 580° C. The results obtained in Examples 1- are shown in Table I.

TABLE I

| Example | Catalyst | Promoter | Percent Conversion | Percent Yield of Butenes | Percent Yield of Butadiene | Total Percent Yield |
| --- | --- | --- | --- | --- | --- | --- |
| 1 | $BaFe_2O_4$ | None | 73 | 32 | 19 | 51 |
| 2 | $BaFe_2O_4$ | ZnO* | 74 | 30 | 24 | 54 |
| 3 | $BaFe_2O_4$ | $MnO_2$* | 86 | 22 | 28 | 50 |
| 4 | $BaFe_2O_4$ | PbO* | 80 | 27 | 26 | 53 |
| 5 | $BaFe_2O_4$ | PbO/ZnO** | 73 | 34 | 24 | 58 |

*Present in amount of 25 weight percent based on total weight of $BaFe_2O_4$ and promoter.
**Mixture of 15 weight percent PbO, 10 weight percent ZnO with mixture present in amount of 25 weight percent based on total Ba ferrite and oxide modifier.

In Examples 2–5, the yield of butadiene was dramatically increased over the yield of butadiene for the control Example 1. In Examples 2, 4 and 5 the total yield of butenes and butadiene were increased in comparison to the total yield of the control Example 1.

EXAMPLES 6 – 8

The procedures of Examples 1 – 5 were repeated with the exception that iron ferrite, $Fe_3O_4$ was used in Example 6 as the catalyst and $Fe_3O_4$ containing CeO was used in Example 7, $Fe_3O_4$ containing PbO and ZnO was used in Example 8. Otherwise, the conditions and process steps were identical to those of Examples 1 – 5. The results obtained from Examples 6 – 8 are shown in Table II.

TABLE II

| Example | Catalyst | Promoter | Percent Conversion | Percent Yield of Butenes | Percent Yield of Butadiene | Total Percent Yield |
|---|---|---|---|---|---|---|
| 6 | $Fe_3O_4$ | None | 82 | 28 | 28 | 56 |
| 7 | $Fe_3O_4$ | CeO* | 83 | 31 | 32 | 63 |
| 8 | $Fe_3O_4$ | PbO/ZnO** | 78 | 28 | 35 | 63 |

*Present in amount of 25 weight percent based on total weight of Fe ferrite and modifier.
**Mixture of 15 weight percent PbO and 10 weight percent ZnO with the mixture being present in amount of 25 weight percent based on total weight of Fe ferrite and the mixture of PbO and ZnO.

Examples 7 and 8 showed increased yields of butadiene as well as total yields of butenes and butadiene in comparison to the control Example 6.

The invention claimed is:

1. A process for the oxidative dehydrogenation of hydrocarbons having 4 to 7 carbon atoms having a stright chain of at least 4 carbon atoms to produce less saturated hydrocarbons of the same number of carbon atoms which comprises contacting, at a temperature of greater than 400°C., said hydrocarbon, a halogen or halogen compound which would liberate halogen said halogen being iodine, bromine or chlorine under the conditions of reaction and from 0.2 to 2.5 moles of oxygen per mole of said hydrocarbon with a catalyst for the dehydrogenation consisting essentially of iron ferrite and 0.35 to 1.3 moles of a metal oxide modifier which is a mixture of ZnO and PbO per mole of iron oxide.

2. A process according to claim 1 wherein the hydrocarbon is selected from the group consisting of n-butane, n-butene and mixtures thereof.

3. A process according to claim 2 wherein the temperature is from 500°C to 600°C.

4. A process according to claim 1 wherein said hydrocarbon is selected from the group consisting of saturated hydrocarbons, monoolefins, diolefins, and mixtures thereof.

5. A process according to claim 4 wherein the hydrocarbon is selected from the group consisting of butene-1, cis-butene-2, trans-butene-2, pentene-1, cis-pentene-2, trans-pentene-2, 2-methyl butene-1, 2-methyl butene-2, 3-methyl butene-1, 2-methyl pentene-1, 2-methyl pentene-2, 2-methyl pentene-3 and mixtures thereof.

\* \* \* \* \*

UNITED STATES PATENT OFFICE
CERTIFICATE OF CORRECTION

PATENT NO. : 3,931,351
DATED : January 6, 1976
INVENTOR(S) : Robert E. Hinkson et al It is certified that error appears in the above-identified patent and that said Letters Patent are hereby corrected as shown below:

Col. 1, line 46, "oxyge," should read -- oxygen, --.

Col. 2, line 7 reads "and barium are known" but should read -- and barium ferrite are known --.

Col. 3, line 6 reads "hydrocarbon fed" but should read -- hydrocarbon feed --.

Col. 3, line 28 reads "such a hydrogen" but should read -- such as hydrogen --.

Col. 4, line 16 reads "will be otained" but should read -- will be obtained --.

Col. 5, line 18 reads " ten square feed" but should read -- ten square feet --.

Col. 6, line 11 reads "are be weight" but should read -- are by weight --.

Col. 7, line 18 reads "a stright chain" but should read -- a straight chain --.

Signed and Sealed this

Twenty-first Day of September 1976

[SEAL]

*Attest:*

RUTH C. MASON
*Attesting Officer*

C. MARSHALL DANN
*Commissioner of Patents and Trademarks*